United States Patent [19]

Ozaki et al.

[11] 4,071,519
[45] Jan. 31, 1978

[54] 1-CARBAMOYL-5-FLUOROURACIL DERIVATIVES

[75] Inventors: Shoichiro Ozaki, Kamakura; Haruki Mori, Yokohama, both of Japan

[73] Assignee: Mitsui Toatsu Chemicals, Incorporated, Tokyo, Japan

[21] Appl. No.: 628,974

[22] Filed: Nov. 5, 1975

[51] Int. Cl.$^2$ .................. C07D 239/10; A61K 31/505
[52] U.S. Cl. .............................. 260/256.4 C; 424/251
[58] Field of Search ................. 260/256.4 C; 424/251

[56] References Cited
PUBLICATIONS

Hoshi, et al., "Pharmacometrics", vol. 3(1), 1969, pp. 57–60.
Hoshi, et al., "Gann", vol. 60, 1969, pp. 115–117.
Owens, "J. Chron. Dis.", vol. 15, 1962, pp. 223–228.
Freireich, et al., "Cancer Chemotherapy Report", vol. 50 (4), 1956, pp. 219–244.
Heidelberger, et al., "Proc. Soc. Exptl. Biol. Med.", vol. 97, 1958, pp. 470–475.

*Primary Examiner*—Nicholas S. Rizzo
*Assistant Examiner*—James H. Turnipseed
*Attorney, Agent, or Firm*—William J. Daniel

[57] ABSTRACT

1-Carbamoyl-5-fluorouracil derivatives represented by the formula

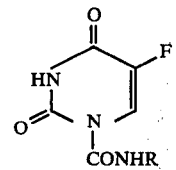

wherein R represents alkyl containing 3–8 carbon atoms are effective oral anti-tumor agents with low toxicity.

7 Claims, No Drawings

1-CARBAMOYL-5-FLUOROURACIL DERIVATIVES

BACKGROUND OF THE INVENTION

1. Field of the Invention

The present invention relates to 5-fluorouracil derivatives and, more particularly, to novel 1-carbamoyl-5-fluorouracils represented by the formula

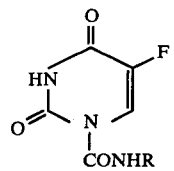

wherein R represents alkyl containing 3-8 carbon atoms, and to their use for tumor therapy.

2. Description of the Prior Art

At the present time, a relatively large number of chemical compounds are recognized for use in clinical therapy for tumors in humans. These anti-tumor agents can be classified into alkylating agents, anti-metabolites, antibiotic anti-tumor agents, hormones, etc. The precise clinical use made of them depends upon the particular kind of tumors, but most of them are employed for acute or chronic leukemia and malignant lymphoma and a few are effective on solid tumors such as adenocarcinoma. Representative of the latter type are 5-fluorouracil and its low toxic derivative 5-fluoro-1-(2-tetrahydrofuryl)-uracil, which are known to be effective on adenocarcinoma. Thus, 5-fluorouracil is well known to be an effective antimetabolite used as an agent for mammary gland or gastrointestinal cancer therapy for humans. However, due to its high toxicity, 5-fluorouracil is not considered a desirable anti-cancer agent and improvement has been recognized as necessary. On the other hand, 5-fluoro-1-(2-tetrahydrofuryl)uracil while of lesser toxicity is substantially inferior to 5-fluorouracil in anti-tumor activity and it has been desired to develop 5-fluorouracil derivatives which are as non-toxic as 5-fluoro-1-(2-tetrahydrofuryl)uracil but are substantially more effective antimetabolites.

In addition most anti-tumor agents, including 5-fluorouracil and 5-fluoro-1-(2-tetrahydrofuryl)uracil, are applied by intravenous administration, resulting in various therapeutical problems for both physicians and patients. Among the reasons these anti-tumor agents are not orally administered is that they are absorbed with difficulty through the stomach and cause intestinal damage as a side effect. Accordingly, it has been desired to develop novel anti-tumor agents which are suitable for oral administration and thus free of these problems.

SUMMARY OF THE INVENTION

The 1-carbamoyl-5-fluorouracils of the present invention are oral anti-tumor agents effective on adenocarcinoma and like tumors, which are significantly superior to existing anti-tumor agents now in clinical use in anti-tumor activity, blood level, retention time and toxicity. The 1-carbamoyl-5-fluorouracils of the present invention are prepared by carbamoylating 5-fluorouracil with an isocyanate or carbamoyl halide.

DESCRIPTION OF THE PREFERRED EMBODIMENTS

The 1-carbamoyl-5-fluorouracils of the present invention have the following general formula

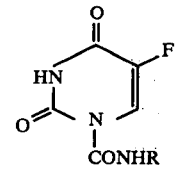

wherein R stands for alkyl containing 3-8 carbon atoms. The number of the carbon atoms in the radical R is important. Thus alkyl radicals containing less than 3 or more than 8 are unfavorable for the purpose of the present invention. Preferred examples of alkyl radicals for R include n-propyl, isopropyl, n-butyl, tert.-butyl, n-pentyl, n-hexyl, n-heptyl and n-octyl.

The compounds of the present invention can be prepared by carbamoylating 5-fluorouracil with an isocyanate having the formula

R—NCO or a carbamoyl halide having the formula

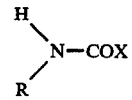

wherein R is as defined above and X is halogen.

The reaction is ordinarily carried out in an organic solvent. Organic solvents such as dimethyl sulfoxide, dimethylformamide, dimethyl acetamide, acetonitrile, and the like are suitable for this purpose. 5-fluorouracil is dissolved in the selected organic solvent, one of the above isocyanates or carbamoyl halides (such as carbamoyl chlorides or bromides) is added to the solution and the reaction mixture is stirred at a temperature ranging from room temperature to the reflux temperature of the reaction mixture. When a carbamoyl halide is employed, the reaction is preferably carried out in the presence of an acid acceptor for the hydrogen halide formed during the reaction. Such acid acceptors include, for example, triethylamine, pyridine, potassium carbonate, sodium bicarbonate, sodium hydride, and the like.

The reaction mixture is preferably filtered off or concentrated under reduced pressure and the obtained crude product is purified, e.g. by washing, recrystallization, and the like methods. The 1-carbamoyl-5-fluorouracils thus obtained are white crystal leaflets or granules and are excellent as oral anti-tumor agents.

The following examples illustrate methods for preparing the 1-carbamoyl-5-fluorouracils of the present invention.

EXAMPLE 1

13.0g (0.10 mole) of 5-fluorouracil was dissolved in 80ml of dimethyl acetamide, then 9.4g (0.11 mole) of n-propyl isocyanate was added thereto at room temperature and stirred at 55° C for 8 hours.

The reaction mixture was concentrated to 50ml by removing dimethyl acetamide and excess n-propyl isocyanate under reduced pressure. After cooling, the residue was poured into 300ml of water, and the resultant precipitate was filtered off. The precipitate was washed with water and ether, respectively, and dried. There was obtained 17.2g (80.1% yield) of 5-fluoro-1-(n-propylcarbamoyl) uracil.

The product was recrystallized from ethanol and there were obtained white crystals melting at 285° C (decomposition) and exhibiting characteristic absorption bands in the infra red region of the spectrum at the following frequencies expressed in reciprocal centimeters: 3400, 3300, 3180, 3808(M), 2970, 2870, 2810, 1720(VS), 1680(S), 1525(S), 1455, 1330, 1270(S), 1213, 1090, 1035, 1005, 935, 845, 785 and 755.

Results of an elementary analysis thereof were well in agreement with the calculated value as follows:

|           | C     | H    | F    | N     |
|-----------|-------|------|------|-------|
| Found (%) | 44.61 | 4.76 | 8.67 | 19.81 |
| Calcd. (%)| 44.65 | 4.65 | 8.84 | 19.53 |
|           | (for $C_8H_{10}FN_3O_3$) | | | |

EXAMPLE 2

13.0g (0.1 mole) of 5-fluorouracil was dissolved in 100ml of dimethyl sulfoxide, then 9.4g (0.11mole) of isopropyl isocyanate was added thereto at room temperature and stirred at the same temperature for 15 hours. The reaction mixture was poured into 800ml of water. The resultant precipitate was filtered off, washed with water and dried to give 14.7g (68.5% yield) of 5-fluoro-1-(iso-propylcarbamoyl)-uracil melting at 275°-285° C (decomposition).

The obtained product exhibited characteristic absorption bands in the infra red region of the spectrum at the following frequencies expressed in reciprocal centimeters: 3300, 3200, 3040, 1740, 1705, 1535, 1465, 1340, 1270, 1165, 1070, 940, 840, 790 and 760.

Results of an elementary analysis thereof were well in agreement with the calculated value as follows.

|           | C     | H    | F    | N     |
|-----------|-------|------|------|-------|
| Found (%) | 44.54 | 4.60 | 9.11 | 19.12 |
| Calcd. (%)| 44.65 | 4.68 | 8.83 | 19.53 |
|           | (for $C_8H_{10}FN_3O_3$) | | | |

EXAMPLE 3

13.0g (0.10 mole) of 5-fluorouracil was dissolved in 70 ml of dimethyl formamide, then 11.9g (0.12 mole) of n-butyl isocyanate was added thereto at room temperature and stirred at the same temperature for 24 hours. The reaction mixture was concentrated to 40ml by removing dimethyl formamide and excess n-butyl isocyanate under reduced pressure. The residue was poured into 300ml of water and resultant precipitate was filtered off. The precipitate was washed and dried and 16.6g (72.3% yield) of 1-(n-butylcarbamoyl)-5-fluorouracil was obtained The product was recrystallized from ethanol and there were obtained white crystals melting at 283° C (decomposition) and exhibiting characteristic absorption bands in the infra red region of the spectrum at the following frequencies expressed in reciprocal centimeters: 3270, 3080, 2950, 2810, 2780, 1715~1740(S), 1685, 1660, 1500~1540, 1480, 1332, 1270, 1205, 1090, 1085, 900, 770 and 750.

Results of an elementary analysis of this product were well in agreement with the calculated value as follows:

|           | C     | H    | F    | N     |
|-----------|-------|------|------|-------|
| Found (%) | 47.29 | 5.32 | 8.18 | 18.80 |
| Calcd. (%)| 47.16 | 5.24 | 8.30 | 18.34 |
|           | (for $C_9H_{12}FN_3O_3$) | | | |

EXAMPLE 4

5.73g (0.0506 mole) of n-pentyl isocyanate, 6.59g (0.0506 mole) of 5-fluorouracil and 20 ml of N, N-dimethylacetamide were mixed together and stirred at 60° C for 12 hours. After the reaction mixture was allowed to stand overnight, the solvent was removed and the residue dissolved in 120 ml of chloroform with the insoluble matter filtered off. The insoluble matter was 4.13 g of unreacted 5-fluorouracil. The obtained solution in chloroform was washed with 2×100 ml of water and dried over sodium sulfate. The solvent was removed and the residue recrystallized from 30 ml of ethanol. There was thus obtained 2.47 g (20.1% based on the n-pentyl isocyanate, or 53.7% based on the 5-fluorouracil converted) of 1-(n-n-pentylcarbamoyl)-5-fluorouracil in the form of white crystals melting at 117.3°–118.0° C.

Results of an elementary analysis thereof were well in agreement with the calculated values as follows:

|           | C     | H    | N     | F    |
|-----------|-------|------|-------|------|
| Found (%) | 49.56 | 5.81 | 16.59 |      |
| Calcd. (%)| 49.38 | 5.80 | 17.28 | 7.81 |
|           | (for $C_{10}H_{14}N_3O_3F$) | | | |

N.M.R. (CDCl$_3$)δ: 0.94 (3H, triplet, —CH$_3$); 1.49 (6H, multiplet, —CH$_2$—); 3.45 (2H, quartet, —CH$_2$NHCO); 8.63 (1H, doublet, CH in the 5-fluorouracil ring); and 9.20 (1H, broad, NH in the 5-fluorouracil ring).

EXAMPLE 5

13.0g (0.10 mole) of 5-fluorouracil was suspended in 60 ml of dimethyl acetamide, then 14.0g (0.11 mole) of n-hexyl isocyanate was added thereto at room temperature and stirred at 50° C for 8 hours. After the reaction mixture was concentrated under reduced pressure, the residue was poured into 400 ml of water and resultant precipitate was filtered off. The precipitate was washed and dried and 19.3g (75.0% yield) of 5-fluoro-1-(n-hexylcarbamoyl)uracil was obtained.

The product was recrystallized from ether and there were obtained white crystals melting at 283° C (decomposition) and exhibiting characteristic absorption bands in the infra red region of the spectrum at the following frequencies expressed in reciprocal centimeters: 3320, 3230, 3080, 2920, 2850, 1720~1740, 1680, 1660, 1510, 1445, 1340, 1272, 1200, 1090, 1042, 802, 770 and 750.

Results of an elementary analysis thereof were well in agreement with the calculated value as follows:

|           | C     | H    | F    | N     |
|-----------|-------|------|------|-------|
| Found (%) | 51.19 | 6.37 | 7.27 | 16.60 |
| Calcd. (%)| 51.36 | 6.23 | 7.39 | 16.34 |
|           | (for $C_{11}H_{16}FN_3O_3$) | | | |

EXAMPLE 6

8.53g (0.066 mole) of 5-fluorouracil, 12.0g (0.085 mole) of n-heptyl isocyanate and 30 ml of N, N-dimethyl acetamide were mixed together and stirred at 60° C for 8 hours. After the reaction mixture was allowed to stand overnight, the solvent was removed under reduced pressure and the residue dissolved in 150 ml of chloroform with the insoluble matter filtered off. There was recovered 2.10 g of unreacted 5-fluorouracil as the insoluble matter. The obtained solution in chloroform was washed with 2×100 ml of water and dried over sodium sulfate. The solvent was removed and the residue recrystallized from 120 ml of ethanol to obtain 7.83 g (43.7% based on the n-heptyl isocyanate, or 58.4% based on the 5-fluorouracil converted) of 1-(N-n-heptylcarbamoyl)-5-fluorouracil as white crystals melting at 102.8°–104.0° C.

Results of an elementary analysis thereof were well in agreement with the calculated values as follows:

|  | C | H | N | F |
|---|---|---|---|---|
| Found (%) | 53.37 | 7.22 | 15.36 | 7.00 |
| Calcd. (%) | 53.13 | 6.69 | 15.49 | |
| (for $C_{12}H_{18}N_3O_3F$) | | | | |

N.M.R. (CDCl$_3$)δ: 0.90 (3H, triplet, —CH$_3$); 1.35 (10H, multiplet, —CH$_2$—); 3.43 (2H, quartet, NH—CH$_2$—); 8.62 (1H, doublet, CH in the 5-fluorouracil ring); and 9.15 (1H, broad, NH in the 5-fluorouracil ring).

EXAMPLE 7

40 ml of dimethyl acetamide was added to 10.01g of 5-fluorouracil and 11.95g of n-octyl isocyanate. After the reaction was carried out at 60° C for an hour, the reaction mixture was allowed to stand overnight at room temperature. The solvent was distilled off and to the residue were added 200 ml of chloroform and 300 ml of water to effect extraction. The chloroform layer was dried over anhydrous sodium sulfate. After evaporating off the chloroform, the precipitated crystals were recrystallized from ethanol to obtain 9.49 g of 1-(N-n-octylcarbamoyl)-5-fluorouracil melting at 98°-100° C.

Results of an elementary analysis thereof were well in agreement with the calculated values as follows:

|  | C | H | N |
|---|---|---|---|
| Found (%) | 55.60 | 7.42 | 14.04 |
| Calcd. (%) | 54.72 | 7.07 | 14.73 |
| (for $C_{13}H_{20}N_3O_3F$) | | | |

N.M.R. (CDCl$_3$), δ 0.89 (3H, triplet, —CH3); 1.32 (12H multiplet, —CH$_2$—); 3.32 (2H, multiplet, NHCH$_2$); 8.48 (1H, doublet, C$_6$—H); 9.28 (1H, triplet, NH); and 12.43 (1H, broad singlet, NH).

The anti-tumor activities of the 1-carbamoyl-5-fluorouracils of the present invention were determined in mice according to the procedure set forth below, and compared with those of 5-fluorouracil (5-FU), 5-fluoro-1-(2-tetrahydrofluryl)uracil (FT-207) and some other analogs.

1×10$^5$ tumor cells of the lymphatic leukemia L-1210 (From the Natural Cancer Institute strain) were inoculated intraperitoneally to BDF$_1$ mice. After 24 hours following the inoculation, a group of six BDF$_1$ mice thus inoculated was forced to receive, once a day, oral administration of 0.1 ml of a suspension of each test compound in 0.5% CMC for 5 days using a stomach tube. The L-1210 strain is in most frequent use in the United States of America having high sensitivity to antimetabolites. There is little fluctuation in survival days of animals inoculated therewith, and definite correlation exists between the number of cells inoculated and the survival days. (In this case the control group died 9 days after the inoculation).

The anti-tumor activity is evaluated in terms of the dosage needed for a given increase in life span (ILS) over that of the control group as calculated by the following formula:

ILS % (% increase in life span) = (T/C × 100−100)% wherein

T: Days from the 1st day of the drug administration until death of treated group of mice, C: Days from the 1st day of the drug administration until death of control group of mice.

"Anti-tumor activity" is compared by taking ILS$_{30}$ (i.e. the dose required for extending the life span by 30%) as the minimum effective dose. The "toxicity" of a given agent can be expressed as its optimal dose (i.e. the dose at which the ILS value reaches its maximum, herein referred to as ILS max), and the relation between "anti-tumor activity" and "toxicity" can be expressed in terms of a "therapeutic index" (T.I.) which is "optimal dose (ILS max value)/minimum effective dose (i.e. ILS$_{30}$ value)". The "therapeutic index" expresses the quantitative spread between the minimum and optimum dosages and thus gives an indication of the relative safety with which an agent can be used.

The results of this test are summarized in the following Tables I and II.

Table I

Anti-tumor Activity[1] of 5-fluorouracil and Selected Derivatives on L-1210 Lymphoid Leukemia

| Dose (mg/kg/day) | 1-Alkyl Carbamoyl-5-Fluorouracil, where Alkyl 15 | | | | | Prior Art | |
|---|---|---|---|---|---|---|---|
| | n-C$_3$H$_7$ | —CH(CH$_3$)$_2$ | —C(CH$_3$)$_3$ | n-C$_4$H$_9$ | n-C$_6$H$_{13}$ | 5-FU | FT-207 |
| 300 | 96 | 110 | | | 150 | | 113 |
| 200 | 110 | 109 | 115 | 120 | 148 | | 116 |
| 100 | 160 | 144 | 154 | 154 | 146 | | 131 |
| 70 | | 156 | 138 | | | 115 | 115 |
| 50 | | | | 138 | 138 | 156 | |
| 30 | 138 | 129 | 126 | 123 | 131 | 133 | 100 |

(Unit: ILS % + 100)

[1]Anti-tumor activity is expressed as the percentage increase in life span, i.e. ILS(T/C) % + 100

As shown in Table I, the anti-tumor activity, expressed as ILS% + 100, of 5-FU and FT-207 reaches 133 and 100 respectively at 30 mg/kg/day, and the optimal doses (ILS/max) of them are 50 and 100 mg/kg/day, respectively; while, the maximum % increase in life span of the compounds of the invention are 1.5-2 times higher than that of FT-207 and at least comparable to that of 5-FU.

Products (Japanese Standards for Antibiotic Medical Supplies).

The results of this test are summarized in the following Table III.

Table II

| | Therapeutic Evaluation[1] of 5-fluorouracil and Selected Derivatives in L-1210 Lymphoid Leukemia System | | | | | | |
|---|---|---|---|---|---|---|---|
| | 1-Alkyl Carbamoyl-5-Fluorouracil, where Alkyl is | | | | | Prior Art | |
| Agent | $n$-$C_3H_7$ | —$CH(CH_3)_2$ | —$C(CH_3)_3$ | $n$-$C_4H_9$ | $n$-$C_6H_{13}$ | 5-FU | FT-207 |
| $ILS_{30}$ (mg/kg/day) | 17 | 30 | 26 | 35 | 30 | 27 | 100 |
| Optimal Dose (mg/kg/day) | 100 | 70 | 100 | 100 | 300 | 50 | 100 |
| ILS max + 100 (%) | 160 | 156 | 154 | 154 | 150 | 156 | 131 |
| Therapeutic Index[2] | 5.9 | 2.3 | 3.8 | 2.9 | 10.0 | 1.9 | 1.0 |

[1]Therapeutic evaluation of each compound was ranked according to the therapeutic index
[2](Optimal dose/$ILS_{30}$).

As can be seen from Table II, all the compounds of this invention reach $ILS_{30}$ at 17-35 mg/kg/day (which result is almost the same as with 5-FU and $ILS_{max}$ (optimal dose) at approximately 100 mg/kg/day. Above all, the compound 1-(N-n-hexylcarbamoyl)-5-fluorouracil exhibits anti-tumor activity over an outstandingly wide dose range of from 30 to 300 mg/kg/day in comparison to 5-FU and FT-207. Furthermore, the compounds of this invention are all superior in T.I. to 5-FU (T.I. = 1.9) and FT-207 (T.I. = 1.0). In particular, 1-N-n-hexylcarbamoyl)-5-fluorouracil shows an especially high T.I. value, i.e. ten times that of FT-207 and five times that of 5-FU, assuring higher safety.

The charge with passage of time in blood levels of the compounds of the invention was measured in rate according to the procedure set forth below, and compared again with that of FT-207 and 5-FU.

Male Wister rats weighing 180-210 g were made to fast for 17 hours and a suspension of each test compound in 0.2% CMC-containing saline was administered orally to the rats at a dose of 100 mg/kg using a stomach tube. After the drug administration the cervical arteriovein of the rat was cut at given intervals of time to collect the whole blood. After being coagulated, the blood was centrifuged to remove the serum. The drug concentration in each serum was measured as 5-FU equivalent by the thin layer cup method using Staphylococcus aureus 209P strain as a standard bacterium. The thin layer cup method was carried out as follows: The standard bacterium cultured on a heart infusion agar plate was so suspended in tript soy broth as to give $O.D._{560} = 0.3$, and kept at 4° C for an hour. The suspension was added to and mixed with Meuller Hinton medium to give a concentration of 2%. Each 5 ml portion of the mixture was poured into a petri dish to make a thin layer plate. A stainless steel cup was fixed on the plate and the serum sample charged into the cup. After 4-hour diffusion at 4° C, the bacterium was incubated at 37° C for 18 hours to measure the diameter of the inhibition zone. Each drug concentration was determined in accordance with II standard Curve Method, Potency Test of Minimum Requirements of Antibiotic Table III

| | | Serum Levels[1] of 5-FU after Oral Administration of Selected 5-FU Derivatives in Rats | | | | |
|---|---|---|---|---|---|---|
| | | | | Time (Hrs.) | | |
| Agent | Dose(mg/kg/day) | 0.5 | 1 | 3 | 6 | 10 |
| $n$-$C_3H_7$ - Deriv. | 100 | 34.13±2.06 | 37.28±6.50 | 14.05±2.37 | 2.70±0.89 | 0.38±0.50 |
| —$CH(CH_3)_2$ - Deriv. | 100 | 14.92±2.42 | 13.72±2.13 | 7.00±1.55 | 0.93±0.64 | <0.04 |
| $n$-$C_4H_9$ - Deriv. | 100 | 22.64±4.31 | 22.80±3.58 | 8.35±1.20 | 1.90±0.64 | 0.63±0.49 |
| $n$-$C_6H_{13}$ - Deriv. | 100 | 5.76±2.67 | 3.04±0.32 | 2.68±1.88 | 2.25±0.22 | 0.59±0.96 |
| 5-FU | 100 | 86.00±3.99 | 3.82±0.89 | 1.20±0.87 | 0.37±0.13* | 0.37±0.11** |
| FT-207 | 100 | 0.24±0.04 | 0.25±0.02 | 0.25±0.02 | 0.22±0.02 | 0.19±0.03 |

[1]Expressed as mcg/ml.
* and ** = the values after five and eight hours, respectively As shown in Table III, FT-207 shows almost constant low serum levels in the range of from 0.2 to 0.25 mcg/ml from 30 minutes until 10 hours following the administration. In the case of 5-FU, the serum levels become extraodinarily high 30 minutes after its administration and fall rapidly in an hour to a level about one-twenty-fifth the 0.5-hour level, indicative of a higher rate of metabolization. In contrast thereto, the compounds of this invention maintain higher serum levels than about 1 mcg/ml (i.e. the minimum serum level required to show substantial anti-tumor activity) up to 10 hours following the administration. In particular, the compound 1-(N-n-hexylcarbamoyl)-5-fluorouracil maintains serum levels 10-20 times as high as those of FT-207 during the 10 hours and therefore, possess excellent pharmacological properties for purposes of clinical use.

From these tests, it can be noted that the compounds of the present invention are distinctly superior to FT-207 and 5-FU in anti-tumor activity, therapeutic index (i.e. safety), blood level and retention time.

What is claimed is:

1. A 1-carbamoyl-5-fluorouracil compound having the formula

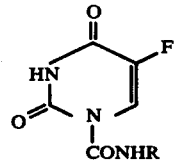

wherein R represents $C_{3-8}$ alkyl.

2. The compound of claim 1 wherein R is an alkyl selected from the group consisting of n-propyl, i-propyl, n-butyl, t-butyl and n-hexyl.

3. 1-(n-hexylcarbamoyl)-5-fluorouracil.

4. 1-(n-propylcarbamoyl)-5-fluorouracil.

5. 1-(t-butylcarbamoyl)-5-fluorouracil.

6. 1-(n-butylcarbamoyl)-5-fluorouracil.

7. 1-(i-propylcarbamoyl)-5-fluorouracil.

* * * * *